United States Patent [19]

Hull et al.

[11] Patent Number: 5,417,719

[45] Date of Patent: May 23, 1995

[54] METHOD OF USING A SPINAL CORD STIMULATION LEAD

[75] Inventors: Vincent W. Hull, Ham Lake; Thomas E. Cross, St. Francis; James P. Langley, Minneapolis, all of Minn.

[73] Assignee: Medtronic, Inc., Minneapolis, Minn.

[21] Appl. No.: 112,025

[22] Filed: Aug. 25, 1993

[51] Int. Cl.$^6$ ............................................. A61N 1/18
[52] U.S. Cl. .................................. 607/46; 607/43; 607/117; 607/148
[58] Field of Search .............. 128/642; 607/43, 46, 607/48, 66, 72, 117, 148, 152

[56] References Cited

U.S. PATENT DOCUMENTS

| | | |
|---|---|---|
| 3,724,467 | 4/1973 | Avery et al. . |
| 4,342,317 | 8/1982 | Axelgaard ............................. 607/43 |
| 4,379,462 | 4/1983 | Borkan et al. . |
| 4,549,556 | 10/1985 | Tarjan et al. . |
| 4,633,889 | 1/1987 | Talalla et al. . |
| 5,067,495 | 11/1991 | Brehm ............................. 607/46 |
| 5,324,322 | 6/1994 | Grill, Jr. et al. ................ 128/642 X |

FOREIGN PATENT DOCUMENTS 0643158  1/1979  U.S.S.R. ............................. 607/148

OTHER PUBLICATIONS

"A serial to Parallel Interface System for Pain Suppression," Proceedings of 7th New England Bioeng. Conf. Troy N.Y. 22–23 Mar., 1979.
Medtronic Resume II Lead, copyright, 1992, pp. 1–25.

Primary Examiner—Lee S. Cohen
Assistant Examiner—Jeffrey R. Jastrzab
Attorney, Agent, or Firm—Curtis D. Kinghorn; Harold R. Patton

[57] ABSTRACT

A lead for providing electrical stimulation signals to the spinal cord and method of use thereof. The lead is implanted in the epidural space and includes an elongate lead paddle located at the distal end of the lead. An array of electrodes is located on the lead paddle. The array has at least three columns of electrodes and includes a column having at least one electrode positioned substantially over the midline of the lead paddle, a column of at least one electrode positioned laterally of the midline on one side thereof and a column of at least one electrode positioned laterally of the midline one the other side thereof. At least one of the columns within the array has more than one electrode. Each of the electrodes is interconnected by a conductor to a respective terminal at the proximal end of the lead. The lead is implanted such that the midline of the of the lead paddle is positioned over the midline of the spinal cord. Each electrode is independently selectable such that the spinal cord may be stimulated unilaterally or bilaterally.

19 Claims, 4 Drawing Sheets

METHOD OF USING A SPINAL CORD STIMULATION LEAD

FIELD OF THE INVENTION

This invention relates to a medical device and method for electrically stimulating the spinal cord. More particularly, the invention is directed to an epidural lead having electrodes at a distal end, the electrodes being configured in an array and being selectable to provide either unilateral or bilateral stimulation.

BACKGROUND OF THE INVENTION

Stimulating the spinal cord for the purpose of controlling pain was first implemented based upon the gate control theory of pain. Simply stated, the gate control theory is based on the premise that activation of large-diameter afferent nerve fibers causes an inhibition of activity in small-diameter nerve fibers. Since small-diameter fibers are involved in the perception of pain their inhibition leads to a consequent inhibition in the perception of pain. As an alternative to the gate control theory some researchers propose that, rather than a physiological gating mechanism, the activation of action potentials in the dorsal columns of the spinal cord leads to a functional blocking of signals in the collaterals of the dorsal columns which, when activated, add to the perception of pain. Under either theory the objectives and principles of spinal cord stimulation for pain control remain the same.

Pain inhibition by activation of large-diameter fibers is directly related to the area or segment of the spinal cord being stimulated. For example, to inhibit pain occurring in the foot, stimulation must activate the large-diameter fibers carrying sensory information from the foot to the spinal cord and higher brain centers. The objective of spinal cord stimulation is to induce sensory paresthesia in such a way that it broadly covers the area in which the patient feels pain. Thus, the proper location of the stimulation electrode is critical to successful pain control.

It is well known that various areas of the body are associated with the dorsal roots of nerve fibers at various spinal segments. Since the dorsal columns receive additional nerve fibers at each spinal segment, the relative position of the nerve fibers from a particular area in the periphery change from the lower spinal segments to the cervical segments. For effective pain control the electrode must be placed adjacent to the spinal column rostral to the dorsal root associated with the painful area.

It is equally well known that stimulation of the dorsal columns at different points medial to lateral will evoke paresthesia perceived as coming from different locations of the body. Additionally, the sensory fibers in the dorsal columns travel to the medulla on the same side of the cord as the peripheral area which they represent. Pain on the right side of the body is treated by placing the electrode to the right of the midline. Pain on the left side of the body is treated by placing the electrode to the left side of the midline. Bilateral pain is treated by placing the electrode on the midline or by placing electrodes on both sides of the midline. Thus, successful pain control through spinal cord stimulation depends on proper positioning of the stimulating electrode both in the longitudinal or rostral-caudal direction and in the lateral to medial direction.

Typically, implantable spinal cord stimulating leads contain multiple electrodes. Two basic styles are available. One style is the percutaneously inserted lead which is introduced through a Touhy needle. The implanting physician places the electrode in an appropriate location using fluoroscopic visualization. The procedure is done under a local anesthetic. Proper electrode placement is tested using a trial stimulation screening technique to assure that paresthesia is perceived in the affected area. An example of this type of lead is disclosed in U.S. Pat. No. 4,379,462 issued to Borkan. That lead has at least three in-line electrodes equally spaced along the distal end of the lead and is designed to be inserted so that the electrodes lie in-line along the spinal cord. Although different pairs of electrodes may be selected so that the area of stimulation may be moved longitudinally along the midline of the spinal cord, there is no provision for stimulating laterally to either or both sides of the midline unless the lead is inserted to one side of midline. In that case once the lead is placed there is no ability to stimulate other than unilaterally on the side of the midline to which the lead is placed. Should the patient later develop the need for bilateral stimulation the physician generally has three options. The physician may reposition the existing lead, implant an additional lead, or remove and replace the existing lead. Percutaneously inserted leads of this type provide focused stimulation patterns and are generally suited for unilateral pain problems. If the pain is bilateral it is often necessary to implant two leads, one on each side of the midline of the spinal cord. The leads may be connected to one pulse generator or to two pulse generators. The use of two leads can cause problems since it is difficult to maintain the relative positions of the leads with respect to one another, both in the longitudinal and lateral directions. Migration of one or both of the leads may result in a loss of paresthesia at the affected location.

The second basic spinal cord stimulation lead type are those surgically implanted through a laminotomy. An example of this type of lead is the RESUME (reg. trademark) lead manufactured by Medtronic, Inc. of Minneapolis, Minn., the assignee of the present invention. This lead has four in-line electrodes located on an elongate paddle at the distal end of the lead. The lead is normally implanted so that the electrodes lie over the midline of the spinal cord. Because leads of this type are surgically implanted, the size of the electrodes may be made larger than those of the percutaneously implanted leads. Various electrode combinations may be selected so that the area of stimulation may be moved along the midline of the spinal cord. The lead provides a broader stimulation pattern more suitable for midline and bilateral pain problems than the percutaneously inserted lead. Since it is surgically implanted it can be sutured to prevent dislodgement and reduce lead migration. In situations where longitudinal placement of the lead over the midline of the spinal cord has not been effective to produce bilateral paresthesia this lead has been placed at an angle with respect to the midline. Once the lead has been inserted at an angle across the spinal cord it is possible, by selection of appropriate electrodes, to stimulate unilaterally on either side of the spinal cord or bilaterally across the spinal cord. However, it is no longer possible to change the stimulation pattern longitudinally along the midline. Additionally, although unilateral stimulation on either side may be provided, the stimulation areas are asymmetric or at different dorsal root levels with respect to the dorsal column. Further, since it is very difficult to maintain the precise angled placement of the lead, any migration of the lead may result in a loss of paresthesia at the affected location.

Another example of a surgically implanted lead is disclosed in U.S. Pat. No. 3,724,467 issued to Avery et al. In one embodiment the lead consists of a flat body portion at the distal end of the lead with electrodes grouped on either side of the longitudinal axis of the lead. The lead is meant to be implanted within the dura and is used for use bilateral stimulation of the spinal cord. In another embodiment the electrodes are mounted on one side of the longitudinal axis of the lead and are meant to provide stimulation to only one side of the spinal cord. In neither embodiment is there any provision for altering the stimulation pattern other than by changing the location of the lead. Thus, once this lead has been implanted there is no way to change the area of stimulation to correct for any loss of paresthesia.

In addition to the problem of lead migration as noted above it is often desirable to effect a change in the area of stimulation in order to vary the effects of paresthesia as the needs of the patient change. The problem of lead migration and the ability to effectively vary the area of stimulation both longitudinally and laterally are areas in which prior art leads have been unable to adequately address. For example, percutaneously inserted leads are difficult to anchor and have a tendency to become dislodged. Even if the initial placement is accurate, lead migration can occur which can adversely affect paresthesia. Additionally, the area in which the patient is experiencing pain can move. Percutaneous leads provide only limited means to change the area of stimulation if the lead migrates or if the needs of the patient change. This is a significant problem with respect to percutaneous leads since the electrodes must be made small enough to fit through a Touhy needle. The area of stimulation is consequently small and even a slight movement of the lead, especially laterally, can adversely affect paresthesia.

Surgically implanted leads are less affected by the problem of lead migration because the electrodes are usually larger and the lead may be stabilized by sutures. However, in instances where lead migration does occur prior art leads have allowed for changes in stimulation only longitudinally along the axis of the lead. There is no mechanism to effect a change of stimulation laterally. The same limitations apply when the needs of the patient change and it becomes desirable to alter the paresthesia. Thus, it would be desirable to have a lead for use in spinal cord stimulation having electrodes which could be selected for stimulation placed such that the area of stimulation could be varied longitudinally, medial to lateral on either side or any combination thereof.

SUMMARY OF THE INVENTION

In accordance with the present invention there is disclosed a lead for providing electrical stimulation to the spinal cord. The lead comprises a flexible lead body having an elongate lead paddle at its distal end. At least four electrodes are positioned on the lead paddle, the electrodes being arranged in at least three columns such that two of the columns have at least one electrode and one of the columns has at least two electrodes. One of the columns is positioned substantially on the midline of the lead paddle, and two of the columns are laterally spaced from the midline of the paddle on opposite sides thereof. At least four terminals are located at the proximal end of the lead body, and at least four conductors lie within the lead body. Each conductor electrically connects one of the electrodes to a respective one of the terminals. The electrodes may be optionally positioned in an orthogonal array concentric about the midline of the lead paddle.

The invention also comprises a method of pain treatment. The method comprises implanting a medical device adjacent the spinal cord. The medical device includes an array of electrodes, the electrodes being arranged in at least three columns. Two of the columns have at least one electrode and one of the columns has at least two electrodes. The method includes positioning the medical device so that at least one of the columns is positioned substantially over the midline of the spinal cord, at least one of the columns is positioned laterally of the midline of the spinal cord on one side thereof and at least one of the columns is positioned laterally of the midline of the spinal cord on the opposite side thereof. Electric signals are applied to at least two of the electrodes to effect pain treatment. The medical device is implanted in the epidural space on the dorsal side of the spinal cord. Optionally, the array of electrodes comprises an orthogonal array concentric about the column positioned over the midline of the spinal cord. In one embodiment the column positioned over the midline of the spinal cord includes at least two electrodes. The method may include applying the electrical signals to different combinations of the electrodes until the most effective electrode stimulation combination for pain control is determined. The most effective electrode stimulation combination includes at least one of unilateral stimulation on one side of the midline of the spinal cord, unilateral stimulation on an opposite side of the midline of the spinal cord, stimulation substantially over the midline of the spinal cord and bilateral stimulation. The method may further comprise implanting a means for applying electrical signals to the electrodes. The means for applying electrical signals may include a pulse generator and a power source. In another embodiment the invention is a method of electrically stimulating the spinal cord for treating pain. The method comprises implanting a lead in the epidural space adjacent the spinal cord, the lead having a lead body with a lead paddle having a plurality of electrodes at a distal end thereof. The electrodes are arranged in an array which includes at least three columns. Two of the columns have at least one electrode and one of the columns has at least two electrodes. One of the columns is positioned substantially on the midline of the lead paddle and two of the columns are laterally spaced from the midline of the lead paddle on opposite sides thereof. A plurality of terminals are located at a proximal end of the lead and a plurality of conductors lie within the lead body interconnecting each electrode with a respective terminal. The method includes positioning the lead so that one of the columns is positioned substantially over the midline of the spinal cord, one of the columns is positioned laterally of the midline of the spinal cord on one side thereof and one of the columns is positioned laterally of the midline of the spinal cord on the opposite side thereof. Electrical signals are applied to at least two of the electrodes to effect pain treatment. In one embodiment the lead is implanted adjacent the dorsal side of the spinal cord. The electrodes in the array may be configured in an orthogonal array concentric about the column positioned substantially over the midline of the spinal cord. The method may include the step of applying the electrical signals to different combinations of said electrodes until the most effective electrode stimulation combination for pain control is determined. The most effective electrode stimulation combination includes at least one of unilateral stimulation on one side of the midline of the spinal cord, unilateral stimulation on an opposite side of the midline of the spinal cord, stimulation substantially over the midline of the spinal cord and bilateral stimulation. The method may further comprise implanting a means for applying electrical signals to the electrodes. The means for applying electrical signals may include a pulse generator and a power source.

In a further embodiment the invention is a method of stimulating the spinal cord with electrical pulses. The method comprises implanting a medical device adjacent the spinal cord. The medical device includes an array of electrodes having at least three columns. Two of the columns have at least one electrode and one of the columns has at least two electrodes. The medical device is positioned so that one of the columns is positioned substantially over the midline of the spinal cord, at least one of said columns is positioned laterally of the midline of the spinal cord on one side thereof and at least one of said columns is positioned laterally of the midline of the spinal cord on the opposite side thereof. Electrical signals are applied to at least two of the electrodes. The medical device may be implanted in the epidural space on the dorsal side of the spinal cord. The array of electrodes may comprise an orthogonal array concentric about the column positioned substantially over the midline of the spinal cord. In a further embodiment the method includes applying the electrical signals to different combinations of the electrodes until a desired electrode stimulation combination is obtained. The desired electrode stimulation combination is the one which is most effective for the application for which the stimulation is being used. The desired electrode stimulation combination includes at least one of unilateral stimulation on one side of the midline of the spinal cord, unilateral stimulation on an opposite side of the midline of the spinal cord, stimulation substantially over the midline of the spinal cord, and bilateral stimulation. The method may further comprise implanting a means for applying electrical signals to said electrodes. The means for applying electrical signals may include a pulse generator and a power source. The medical device used in the method may comprise a lead having a lead body with a plurality of electrodes at a distal end. The lead includes a plurality of terminals at a proximal end and a plurality of conductors within the lead body interconnecting each electrode with a respective terminal.

BRIEF DESCRIPTION OF THE DRAWINGS

The foregoing and other aspects of the present invention will be best appreciated with reference to the detailed description of the invention, which follows, when read in conjunction with the accompanying drawings wherein.

DETAILED DESCRIPTION OF THE INVENTION

Figure 1:
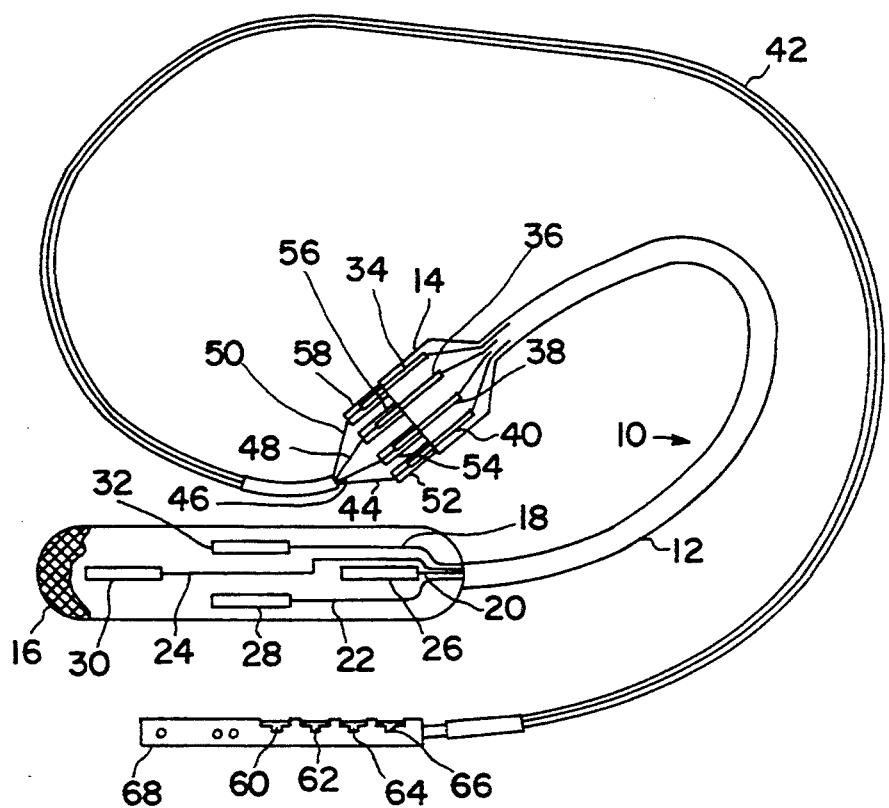
FIG. 1 is a plan view of one embodiment of the neurological stimulation lead of the present invention.

FIG. 1 is a plan view of one embodiment of the neurological stimulation lead of the present invention. Lead 10 includes a lead body 12 connected at its proximal end to a flat connector 14 and at its distal end to a lead paddle 16. Lead body 12 is made of a physiologically inert material such as silicone rubber and has a single lumen which encloses a plurality of conductors 18, 20, 22, and 24. Conductors 18, 20, 22, and 24 interconnect a plurality of electrodes 26, 28, 30 and 32 located on lead paddle 16 with respective stainless steel pins or terminals 34, 36, 38 and 40 which are molded into flat connector 14 which is made of silicone rubber. Conductors 18, 20, 22 and 24 are made of an appropriate electrically conductive material such as stranded stainless steel and are separately insulated with an appropriate insulating material. Preferably, they are coated with polytetrafluoroethylene (PTFE).

As further illustrated in FIG. 1, lead 10 is connected to a percutaneous extension 42. Percutaneous extension 42 includes a plurality of separately insulated electrically conductive wires 44, 46, 48 and 50. At the distal end of extension 42 wires 44, 46, 48 and 50 are molded into silicone sleeves 52, 54, 56 and 58 in a manner which brings them into electrical contact with terminals 34, 36, 38 and 40. At the proximal end the wires are connected to separate contacts 60, 62, 64 and 66 which are held within a pin connector 68. Pin connector 68 is used to connect the lead to an external pulse generator in order to perform a percutaneous screening procedure to determine correct lead placement and electrode combination in a manner that will be described more fully hereafter.

Figure 2:
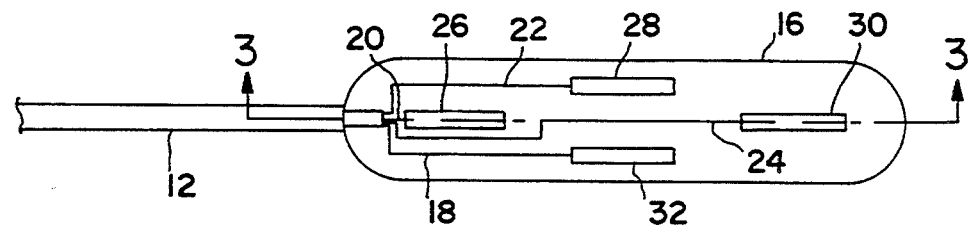
FIG. 2 is an elevational view of the distal portion of the lead of FIG. 1.
Figure 3:
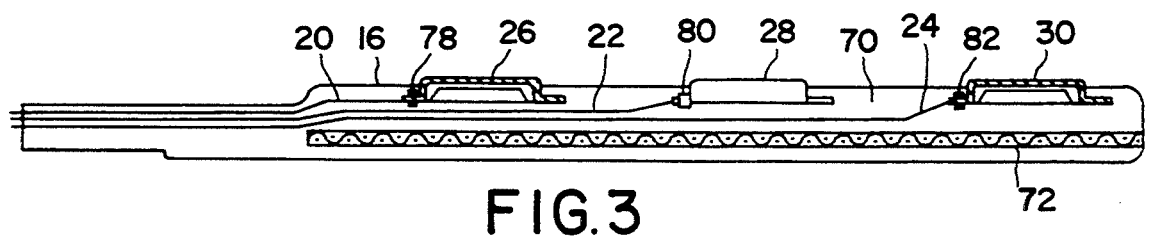
FIG. 3 is a cross sectional view in side elevation of the distal portion of the lead of FIG. 2 taken along line 3—3.

FIGS. 2 and 3 are top and cross sectional side views, respectively, of the distal end of lead 10 illustrating the shape and configuration of electrodes 26, 28, 30 and 32 on lead paddle 16. As best seen in FIG. 3, lead paddle 16 is comprised of molded transparent silicone rubber portion 70 surrounding a mesh portion 72 made of DACRON ®, a polyester material made by E. I. du Pont de Nemours & Co. The electrodes are embedded within rubber portion 70 and protrude slightly above the surface of lead paddle 16 in order to enhance their tissue stimulation effectiveness. Conductors 20, 22 and 24 are welded to the distal ends of electrodes 26, 28 and 30, respectively, and are crimped at ferrules 78, 80 and 82 which provide strain relief. Conductor 18, not seen in FIG. 3, connects in a similar manner to electrode 32. Electrodes 26, 28, 30 and 32 may be of any desired shape or size such as round or oval although the elongate shape as shown in the drawings has been found to be particularly effective. In the embodiment shown, each electrode is a 2 mm×6 mm oval with a surface area equal to approximately 12 square mm. In this embodiment an orthogonal electrode array is formed comprising a center column with two electrodes positioned along the midline of lead paddle 16 and two lateral columns, each lateral column having one electrode positioned off of the midline. The spacing of the electrodes along the midline should be such that when the lead is properly positioned the dorsal roots at two segments of the dorsal column may be stimulated. The spacing between the laterally positioned electrodes and the midline should be in the range of from 1 mm to 5 mm and preferably in the range of from 1 mm to 3 mm. In the embodiment shown, the dimension of lead paddle 16 is approximately 44 mm×10 mm and the distance between electrodes 26 and 30, which are centered over the midline, is 19 mm. Laterally spaced electrodes 28 and 32 are equidistantly spaced from the midline and are spaced a distance of 2 mm from the midline.

Figure 1A:
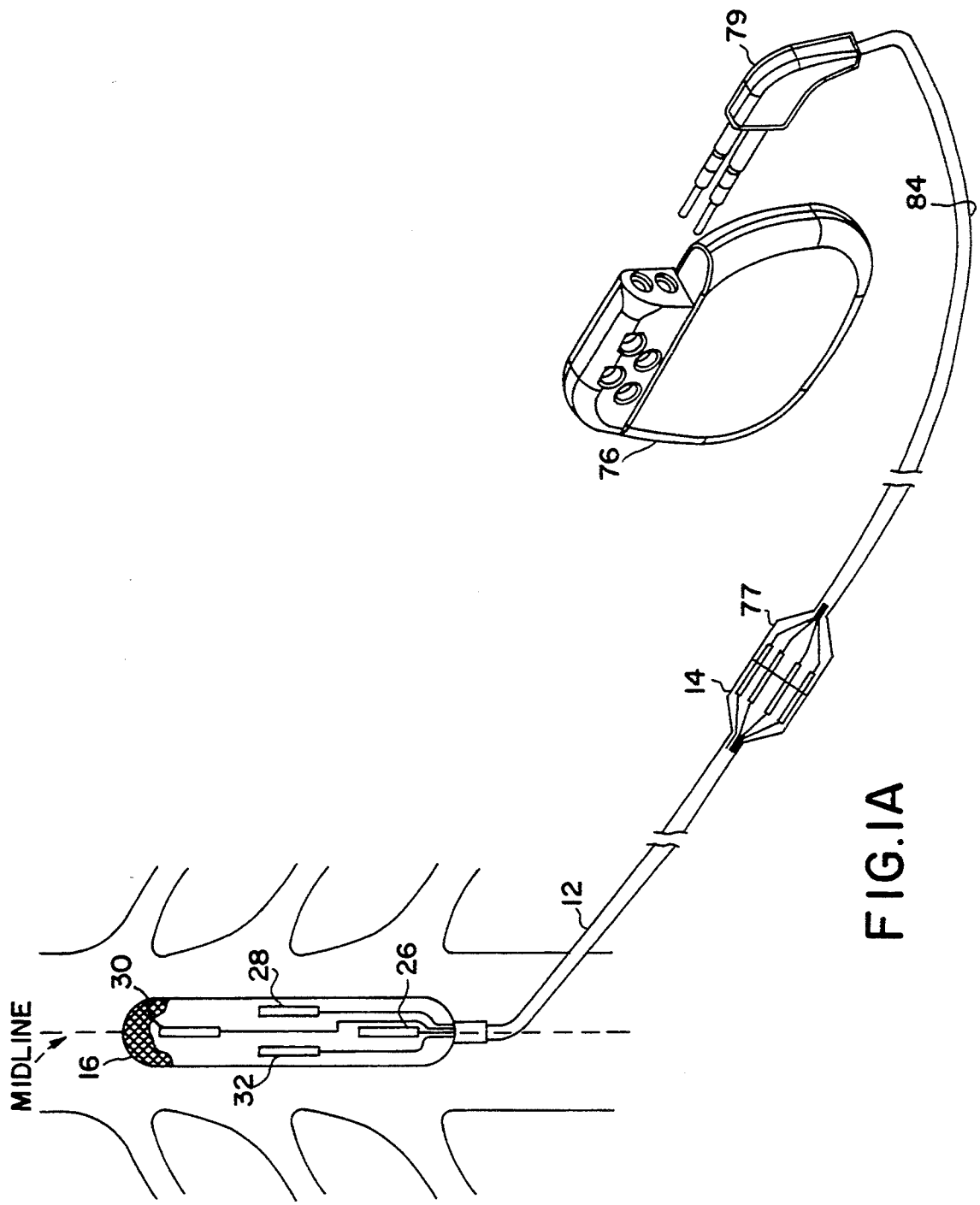
FIG. 1A is a partial schematic view of the spinal cord of a patient with the implanted neurological stimulation lead of FIG. 1 connected to a pulse generator.
Figure 4:
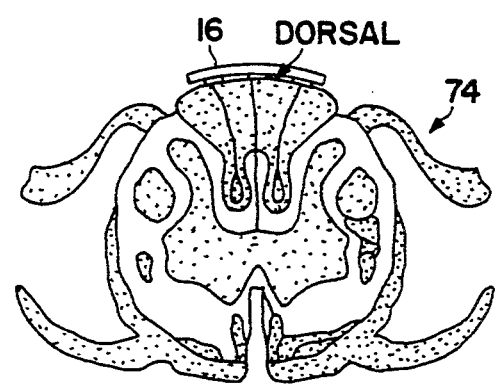
FIG. 4 is a cross sectional view schematically illustrating the spinal column of a patient with the lead of FIG. 1 positioned of the dorsal side thereof.
Figure 5:
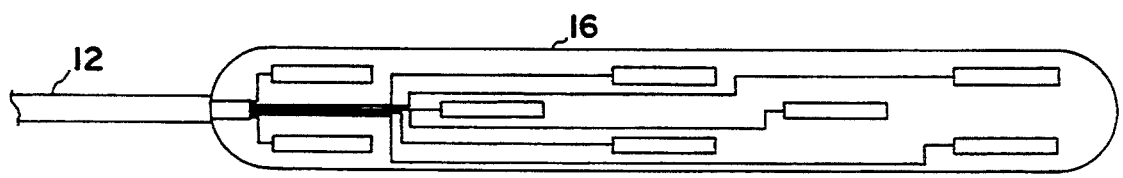
FIGS. 5, 6, 7, 8 and 9 are plan views of the distal portion of a neurological stimulation lead in accordance with alternate embodiments of the invention.
Figure 6:
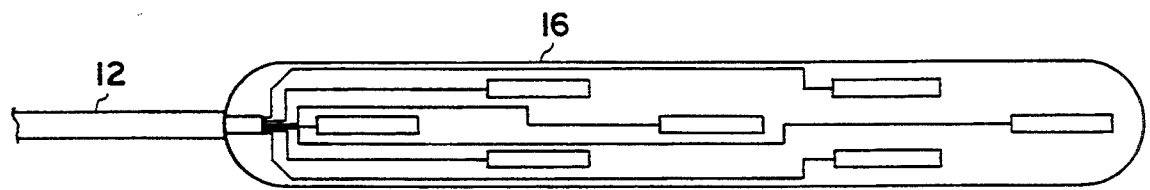
Figure 7:
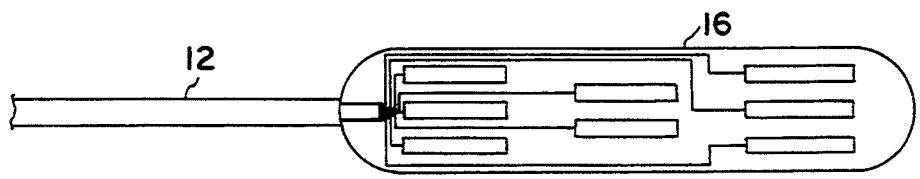
Figure 8:
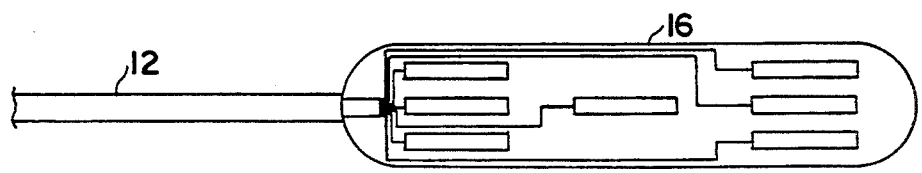
Figure 9:
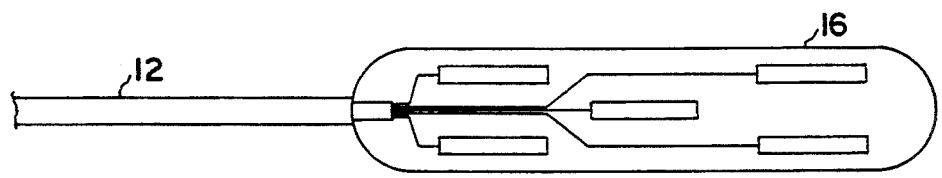

As shown in FIGS. 1A and 4 lead 10 is adapted to be implanted in a human patient along the dorsal side of the spinal column 74. As best seen in FIG. 1A, the lead is implanted so that electrodes 26 and 30 are over the midline of the spinal cord. Each electrode is independently selectable so that when the lead paddle 16 is positioned as shown a variety of stimulation patterns may be selected by providing stimulation signals to two or more of the electrodes. The stimulation signals or pulses are provided by an external pulse generator during the screening procedure. After the initial electrode combination is selected, the lead is connected to an implanted pulse generator 76 by a lead extension 84. Lead extension 84 has a flat connector 77 at its distal end which connects to flat connector 14 and has a plug-in connector 79 at its proximal end which connects to pulse generator 76. Pulse generator 76 may be a fully implanted system such as the "ITREL II" pulse generator available from Medtronic. Inc. or may employ a partially implanted radio-frequency system such as the "XTREL" system also available from Medtronic, Inc.

In use, the lead is designed to be implanted in the epidural space after the dura has been exposed by a partial laminectomy. Although the invention will be described primarily in connection with its implantation in the epidural space along the dorsal column for use in stimulating the spinal cord as a method of treating pain, it should be noted that the electrode may be used for any spinal cord stimulation application such as stimulation to induce motor function or to inhibit spasticity. When used for such other applications the lead may be implanted laterally or on the ventral side of the spinal column. The lead is also suitable for use in applications other than spinal cord stimulation such as stimulation of peripheral nerves.

Once the lead has been implanted a screening procedure is performed to determine if the position of the lead will adequately supply paresthesia to the desired location. During the screening process, various electrode combinations are tested until the right combination is achieved. By using the lead of the present invention various unilateral and/or bilateral stimulation combinations are possible. For example, if electrical signals are provided to electrodes 26 and 30 the stimulation area will be along the midline of the spinal cord. Unilateral stimulation may be achieved by providing signals to electrodes 26 and 28, to electrodes 26, 28 and 30, to electrodes 26 and 32, or to electrodes 26, 32 and 30. Similarly, bilateral stimulation may be achieved by providing signals to electrodes 32 and 28, to electrodes 32, 28 and 26, or to electrodes 32, 30 and 28. A total of 65 different electrode stimulation combinations are available for the four electrode array shown in shown if FIGS. 1 through 4 by selecting different electrode and stimulation polarity combinations. Thus, the lead of the present invention provides a substantial amount of flexibility in achieving a stimulation pattern which is moveable longitudinally and laterally along the spinal column and which is effective in supplying paresthesia even if the area of pain changes or there is migration of the lead.

After the screening process is completed and the lead is properly anchored in place the lead disconnected from the external screening device and connected to the implanted pulse generator so that the entire system can be internalized. This is done by cutting silicone sleeves 52, 54, 56 and 58 to disconnect percutaneous extension 42. Lead extension 84 is then connected to fiat connector 14 in a manner not shown but well known to those skilled in the art.

Once the stimulation system including lead 10 has been internalized the lead of the present invention provides the flexibility to make modifications to the area of paresthesia should the needs of the patient change or should there be any lead migration. This is done by changing the electrode combinations by external programming procedures well known in the art. Thus, the need for repositioning or removing the lead is greatly reduced.

FIGS. 5, 6, 7, 8 and 9 illustrate various alternative embodiments of the present invention. These embodiments show different electrode arrays in which the number and location of the electrodes on lead paddle 16 is varied. Each of the embodiments includes a column having at least one electrode positioned substantially over the midline of lead paddle 16, a column of at least one electrode positioned laterally of the midline on one side thereof and a column of at least one electrode positioned laterally of the midline one the other side thereof. At least one of the columns within the array has more than one electrode. Within that specific design criteria it can be seen that any number of electrode arrays can be utilized within the scope of the present invention having varying numbers of electrodes and varying numbers of electrode columns. The position of the electrodes within the array need not be symmetric nor concentric about the midline of the lead paddle nor comprise an orthogonal array as shown in the embodiments although such configurations are preferred and have been found to be particularly effective in establishing desirable stimulation patterns.

From the foregoing detailed description of specific embodiments of the invention, it should be apparent that a neurological stimulation lead for spinal cord stimulation has been disclosed. Although several particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. For instance, the choice of materials or variations in the shape of the lead paddle or electrodes or electrode array are believed to be a matter of routine for a person of ordinary skill in the art with knowledge of the embodiments disclosed herein. Likewise, although the embodiments disclosed relate primarily to spinal cord stimulation for treatment of pain, the stimulation lead disclosed herein could be used for other applications such as nerve stimulation for control of motor function.

We claim:

1. A method of pain treatment comprising:
    implanting a medical device adjacent a spinal cord having a dorsal side, said medical device including an array of electrodes, said electrodes being arranged in at least three columns, two of said columns having at least one electrode and one of said columns having at least two electrodes,
    positioning said medical device so that at least one of said columns is positioned substantially over the midline of the spinal cord, at least one of said columns is positioned laterally of the midline of the spinal cord on one side thereof and at least one of said columns is positioned laterally of the midline of the spinal cord on the opposite side thereof, and
    applying electric signals to at least two of said electrodes to effect pain treatment.

2. The method of claim 1 wherein said method further comprises the step of implanting said medical device in epidural space on a dorsal side of the spinal cord.

3. The method of claim 1 wherein said array of electrodes comprises an orthogonal array concentric about said column positioned over the midline of the spinal cord.

4. The method of claim 1 wherein said column positioned over the midline of the spinal cord includes at least two electrodes.

5. The method of claim 1 wherein the step of applying electric signals includes applying said electric signals to different combinations of said electrodes until the most effective electrode stimulation combination for pain control is determined.

6. The method of claim 5 wherein the step of applying electric signals includes applying electric signals to cause stimulation, said stimulation occurring in areas chosen from the group consisting of stimulation on one side of the midline of the spinal cord, unilateral stimulation on an opposite side of the midline of the spinal cord, stimulation substantially over the midline of the spinal cord and bilateral stimulation.

7. The method of claim 1 further comprising the step of implanting a means for applying said electric signals to said electrodes.

8. A method of electrically stimulating a spinal cord for treating pain comprising:
    implanting a lead in epidural space adjacent the spinal cord, said lead having a lead body with a lead paddle having a plurality of electrodes at a distal end thereof and a midline, said electrodes being arranged in an array including at least three columns, two of said columns having at least one electrode and one of said columns having at least two electrodes, one of said columns being positioned substantially on the midline of said paddle, and two of said columns being laterally spaced from the midline of said paddle on opposite sides thereof, a plurality of terminals at a proximal end thereof and a plurality of conductors within said lead body interconnecting each electrode with a respective terminal,
    positioning said lead so that one of said columns is positioned substantially over the midline of the spinal cord, one of said columns is positioned laterally of the midline of the spinal cord on one side thereof and one of said columns is positioned laterally of the midline of the spinal cord on the opposite side thereof, and
    applying electrical signals to at least two of said electrodes to effect pain treatment.

9. The method of claim 8 wherein the method includes the step of implanting said lead adjacent a dorsal side of the spinal cord.

10. The method of claim 8 wherein said electrodes are configured in an orthogonal array concentric about said column positioned substantially over the midline of the spinal cord.

11. The method of claim 8 wherein the method includes the step of applying said electrical signals to different combinations of said electrodes until the most effective electrode stimulation combination for pain control is determined.

12. The method of claim 11 wherein the step of applying electric signals includes applying electric signals to cause stimulation, said stimulation occurring in areas chosen from the group consisting of stimulation on one side of the midline of the spinal cord, unilateral stimulation on an opposite side of the midline of the spinal cord, stimulation substantially over the midline of the spinal cord and bilateral stimulation.

13. The method of claim 8 further comprising the step of implanting a means for applying said electrical signals to said electrodes.

14. A method of stimulating a spinal cord with electrical pulses comprising:
    implanting a medical device adjacent the spinal cord, said medical device including an array of electrodes having at least three columns, two of said columns having at least one electrode and one of said columns having at least two electrodes,
    positioning said medical device so that one of said columns is positioned substantially over the midline of the spinal cord, at least one of said columns is positioned laterally of the midline of the spinal cord on one side thereof and at least one of said columns is positioned laterally of the midline of the spinal cord on the opposite side thereof, and
    applying electrical signals to at least two of said electrodes.

15. The method of claim 14 wherein said method further comprises the step of implanting said medical device in epidural space on a dorsal side of the spinal cord.

16. The method of claim 14 wherein said array of electrodes comprises an orthogonal array concentric about said column positioned substantially over the midline of the spinal cord.

17. The method of claim 14 wherein the method includes the step of applying said electrical signals to different combinations of said electrodes until a desired electrode stimulation combination is obtained.

18. The method of claim 17 wherein the step of applying electric signals includes applying electric signals to cause stimulation, said stimulation occurring in areas chosen from the group consisting of stimulation on one side of the midline of the spinal cord, unilateral stimulation on an opposite side of the midline of the spinal cord, and stimulation substantially over the midline of the spinal cord.

19. The method of claim 14 further comprising the step of implanting a means for applying said electrical signals to said electrodes.

* * * * *